United States Patent [19]
Kuck et al.

[11] Patent Number: 5,921,923
[45] Date of Patent: Jul. 13, 1999

[54] METHOD FOR LOCATING ACCESSORY PATHWAYS IN THE HEART USING MULTIPLE PAIRS OF SENSING ELECTRODES

[75] Inventors: Karl Heinz Kuck, Hamburg, Germany; Russell B. Thompson, Menlo Park, Calif.

[73] Assignee: EP Technologies, Inc., Sunnyvale, Calif.

[21] Appl. No.: 08/814,604

[22] Filed: Mar. 10, 1997

Related U.S. Application Data

[63] Continuation of application No. 08/672,245, Jun. 28, 1996, abandoned, which is a continuation of application No. 08/139,582, Oct. 19, 1993, abandoned.

[51] Int. Cl.$^6$ ........................................................ A61N 1/06
[52] U.S. Cl. ........................... 600/373; 607/99; 607/122
[58] Field of Search .............................. 600/373; 607/98, 607/99, 122, 125, 126

[56] References Cited

U.S. PATENT DOCUMENTS

| | | | |
|---|---|---|---|
| 4,630,611 | 12/1986 | King | 128/642 |
| 4,848,352 | 7/1989 | Pohndorf et al. | 128/642 |
| 4,892,102 | 1/1990 | Astrinsky | 128/642 |
| 5,081,990 | 1/1992 | Deletis | 128/642 |
| 5,156,151 | 10/1992 | Imran | 128/642 |
| 5,172,694 | 12/1992 | Flammang et al. | 128/642 |
| 5,228,441 | 7/1993 | Lundquist | 128/642 |
| 5,385,146 | 1/1995 | Goldreyer | 128/642 |
| 5,433,198 | 7/1995 | Desai | 607/122 |

FOREIGN PATENT DOCUMENTS 5023399 2/1993 Japan ................................. 607/122

*Primary Examiner*—Brian L. Casler
*Attorney, Agent, or Firm*—Lyon & Lyon LLP

[57] ABSTRACT

A multiple electrode array senses electrical events in heart tissue at different orientations in a localized region. First, second, and third electrode elements are spaced apart along different axes. The electrodes are electrically isolated from each other. The spaced apart and electrically isolated electrodes sense multiple bipolar signals measured along the different axes. The electrode array can, without changing position, continuously record multiple electrical events at different relative orientations within a localized area. The spacing and orientation of electrodes on the array permit the physician to detect a small volume signal (like one associated with an accessory pathway) and to differentiate it from nearby large volume signals (like those associated with atrial and ventricular potentials).

3 Claims, 5 Drawing Sheets

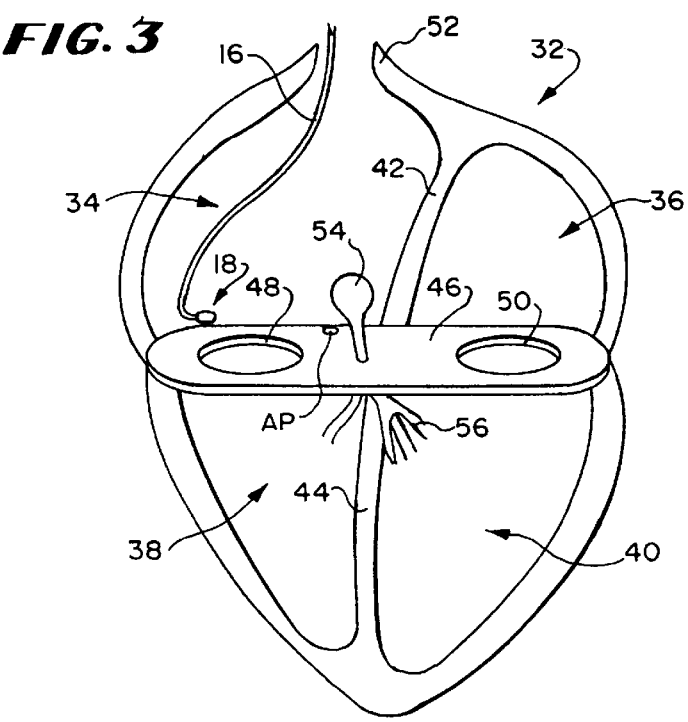
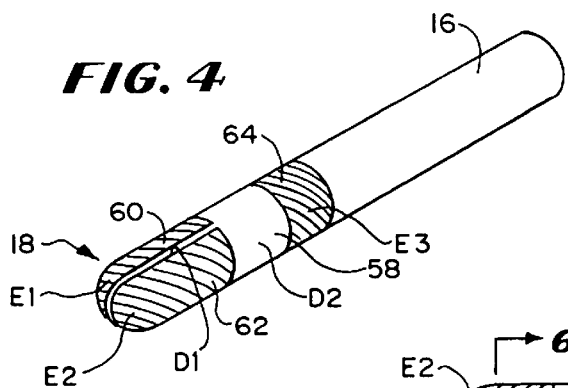
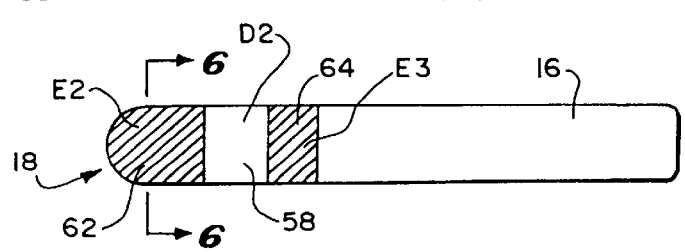
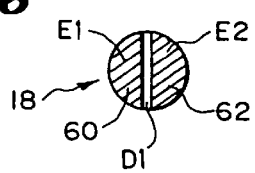

FIG. 9
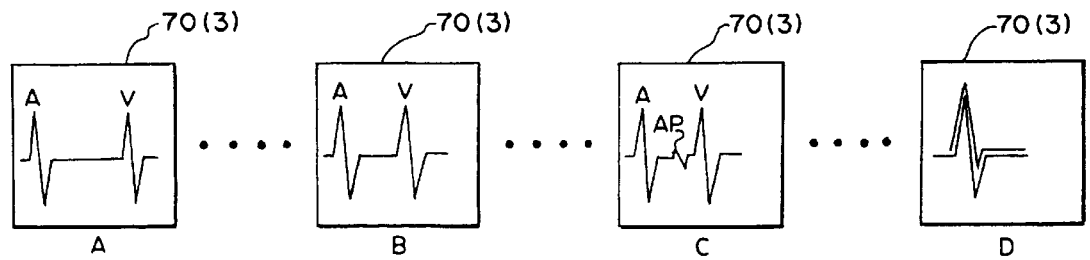
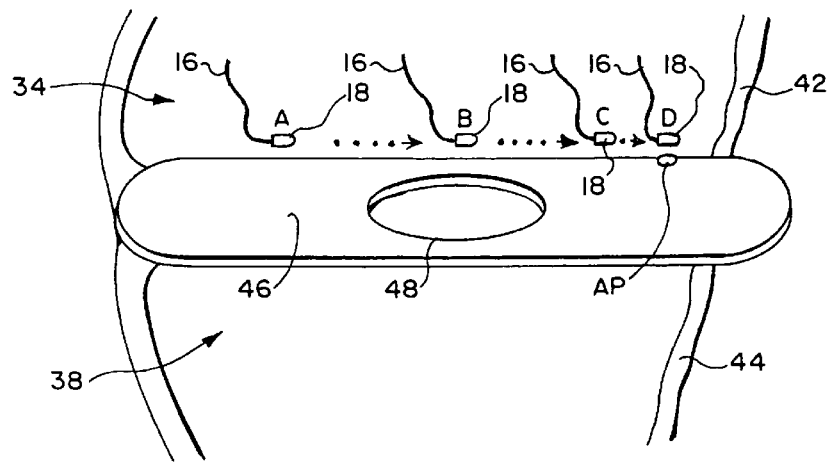
FIG. 10
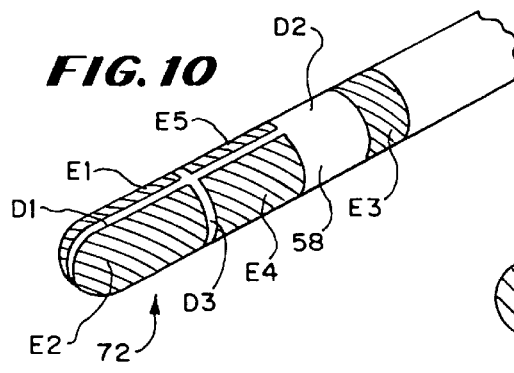
FIG. 11
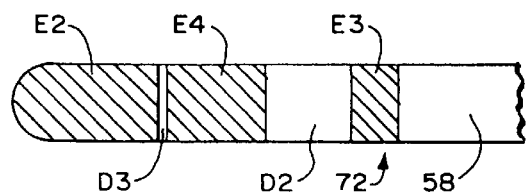

METHOD FOR LOCATING ACCESSORY PATHWAYS IN THE HEART USING MULTIPLE PAIRS OF SENSING ELECTRODES

This is a continuation of application(s) Ser. No. 08/672,245 filed on Jun. 28, 1996 now abandoned which is a continuation of application Ser. No. 08/139,582 filed Oct. 19, 1993 now abandoned.

FIELD OF THE INVENTION

The invention is directed to systems and methods for mapping and ablating the interior regions of the heart for treating cardiac conditions.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular (AV) groove. This propagation causes the atria to contract.

At the atrioventricular (AV) groove, the impulse encounters the so-called "skeleton" of the heart. Here, a fibrous structure separates the atria from the ventricles. The rings or annuli of the tricuspid valve (between the right atrium and right ventricle) and the mitral (or bicuspid) valve (between the left atrium and the left ventricle) are attached to this fibrous skeleton.

The fibrous skeleton is electrically inert. It normally acts as an insulator to block the conduction of the impulse from the AV node. The electrical impulse would be prevented from crossing over to the ventricular side of the AV groove, if not for the specialized AV conducting tissue, called the atrioventricular node (or "AV node") and the bundle of HIS (or "HIS bundle").

The AV node slows the conduction of the impulse to the ventricles, allowing the atria to first complete their contraction and empty blood from the atria into the ventricles. The slowed impulse eventually enters the HIS bundle, which delivers the impulse to the ventricular side. The ventricles then contract.

The AV conduction system results in the described, organized sequence of myocardial contraction.

Normally, the AV conduction system is the only way for electrical impulses to be conducted from the atria to the ventricles. However, some people are born with additional electrical conduction paths between the atria and ventricles. These extra connections are called "bypass tracts" or "accessory pathways." Accessory pathways consist of tiny bands of myocardial tissue that most commonly insert in atrial muscle on one end and ventricular muscle on the other end. The most common variety is located along the AV groove.

Accessory pathways offer a potential parallel route for electrical impulses, bypassing the normal AV conduction system.

The accessory pathways do not slow down the electrical impulse, like the AV node does. Instead, the accessory pathways conduct impulses more quickly, like myocardial tissue. When they conduct the impulses in the antegrade direction (i.e., from the atria to the ventricles), they precede the normal impulse from AV node, causing premature stimulation and contraction of the ventricles. When they conduct the impulses in the retrograde direction (i.e., from the ventricles to the atria), the atria contract after the ventricles do. In either case, normal heart rhythm becomes disrupted.

Patients with accessory pathways are susceptible to reentrant tachycardias involving both the AV node and the accessory pathway. the resultant fast heart rate can be potentially life-threatening. The elevated heart rate can lead to serious hemodynamic compromise. Sudden syncope or hemodynamic collapse can occur.

Accessory pathways are generally invisible to the naked eye. They therefore must be located by their electrophysiologic effects. Catheter-based techniques have been developed to record accessory pathway activation by mapping along the AV groove. The conventional mapping techniques typically use a pair of bipolar sensing electrodes to record activation potentials. The sensing electrodes are carried by catheters introduced by vascular access into the heart. These catheter-based techniques have allowed identification of the site of the accessory pathway. Once identified, the conduction block caused by the accessory pathway can be cleared by catheter-based thermal ablation techniques.

FIG. 1 shows a typical electrogram showing the initiation of a normal atrial complex A followed by the initiation of a normal ventricular complex V. FIG. 1 also shows a typical complex associated with an accessory pathway AP, which occurs between the atrial complex A and the ventricular complex V. FIG. 1 shows how relatively small the AP complex is, compared to the atrial and ventricular complexes A and V. FIG. 1 also shows how relatively closely spaced in terms of time (measured in milliseconds) the AP complex is to the ventricular complex V. This time difference is typically only about 20 to 36 milliseconds.

For these reasons, physicians frequently find it difficult to locate the accessory pathway (AP) activation potentials using conventional bipolar sensing techniques.

Conventional bipolar electrodes are not very sensitive to small volume, far-field signals, like those associated with accessory pathways. Often, the AP activation potentials become fused with the local ventricular potentials V. As a result, physicians cannot differentiate between the potentials with enough certainty to positively locate the site of the accessory pathway.

Furthermore, far-field signals will be missed if the bipolar electrodes are oriented perpendicular to the signal path. As a result, many complex movements are presently required to map the AV groove, as the physician must continuously change the orientation of conventional bipolar electrodes to assure that the far-field activation signals are not missed. The difficulties involved in manipulating the electrodes within the heart are significant, as they must be controlled remotely while relying on using indirect fluoroscopic imaging. Stable and intimate contact between the myocardial tissue and the mapping electrodes are often difficult to achieve and maintain.

As a result, the location of accessory pathways using conventional catheter-based techniques are difficult and time consuming. For these reasons, many attempts at creating curative lesions ultimately fail.

There is a need for catheter-based systems and methods that permit the physician to record multiple electrical events at different relative orientations within a localized area without continuous positioning and repositioning.

There is also a need for catheter-based systems and methods that permit the physician to detect a small volume, far-field signal (like one associated with an accessory pathway), even in the presence of large volume, near field signals (like those associated with atrial and ventricular potentials).

SUMMARY OF THE INVENTION

One aspect of the invention provides a multiple electrode array for sensing electrical events in localized regions of heart tissue. The array comprises at least three, mutually spaced apart electrode elements. The spaced apart elements are also electrically isolated one from the other, so that bipolar signal readings can be obtained between selected electrode pairs.

According to the invention, the first electrode element is spaced from the second electrode element along a first axis. The third electrode element is spaced from the first and second electrode means along a second axis that extends at an angle to the first axis. In a preferred embodiment, the first and second axes are orthogonal to each other.

Signal wires electrically coupled to the first, second, and third electrode elements convey bipolar signals measured along different axes between different pairs of the electrodes. The signal wires convey a first bipolar signal measured along the first axis between the first and second electrodes. The signal wires also convey second and third bipolar signals measured along the second axis between the first and third electrodes and between the second and third electrodes. The electrode array can, without changing position, continuously record multiple electrical events at different relative orientations, all within a localized area.

The spacing and orientation of electrodes on the array permit the physician to detect a small volume signal (like one associated with an accessory pathway) and to differentiate it from nearby large volume signals (like those associated with atrial and ventricular potentials).

In a preferred embodiment, the first and second electrode elements comprise electrode segments that are diametrically spaced apart along the first axis. In this embodiment, the third electrode element comprises a ring electrode spaced from the opposite electrode segments along the second axis.

In a preferred embodiment, the electrode array is carried at the distal end of a catheter guide body. A handle at the proximal end of the guide body permits the physician to remotely manipulate the electrode array within the body.

Another aspect of the invention provides a method of sensing electrical events in heart tissue using the above described electrode array. The method establishes contact between a region of heart tissue and the electrode array. The method continuously maintains the contact between the electrode array and heart tissue region while (i) measuring the first bipolar signal between the first and second electrodes; (ii) measuring the second bipolar signal between the first and third electrodes; and (iii) measuring the third bipolar signal between the second and third electrodes. The method analyzes the first, second, and third bipolar signals, preferably by means of electrogram displays.

In a preferred embodiment, the method allows for easy and unambiguous recording of accessory pathway potentials so that the accessory pathway(s) can be ablated.

BRIEF DESCRIPTION OF THE DRAWINGS

FIG. 3 is a diagrammatic view of the heart showing the deployment of electrode array to locate an accessory pathway along the AV groove;

FIG. 4 is a front perspective view of an electrode array that embodies the features of the invention;

FIG. 5 is a side view of the electrode array shown in FIG. 4;

FIG. 6 is a front section view of the electrode array taken generally along line 6—6 in FIG. 5;

FIG. 9 is a view of the movement of the electrode array shown in FIGS. 4 to 6 along the AV groove and the resulting change in electrogram morphologies as the site of the accessory pathway is determined according to the invention;

FIG. 10 is a front perspective view of an alternative electrode array that embodies the features of the invention;

FIG. 11 is a side view of the electrode array shown in FIG. 10; and

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
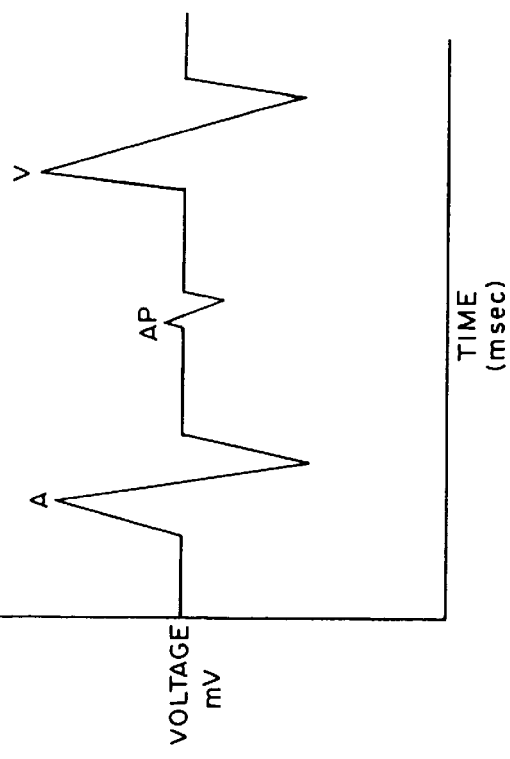
FIG. 1 is a diagrammatic view of a representative electrogram showing atria, ventricular, and accessory pathway complexes.
Figure 2:
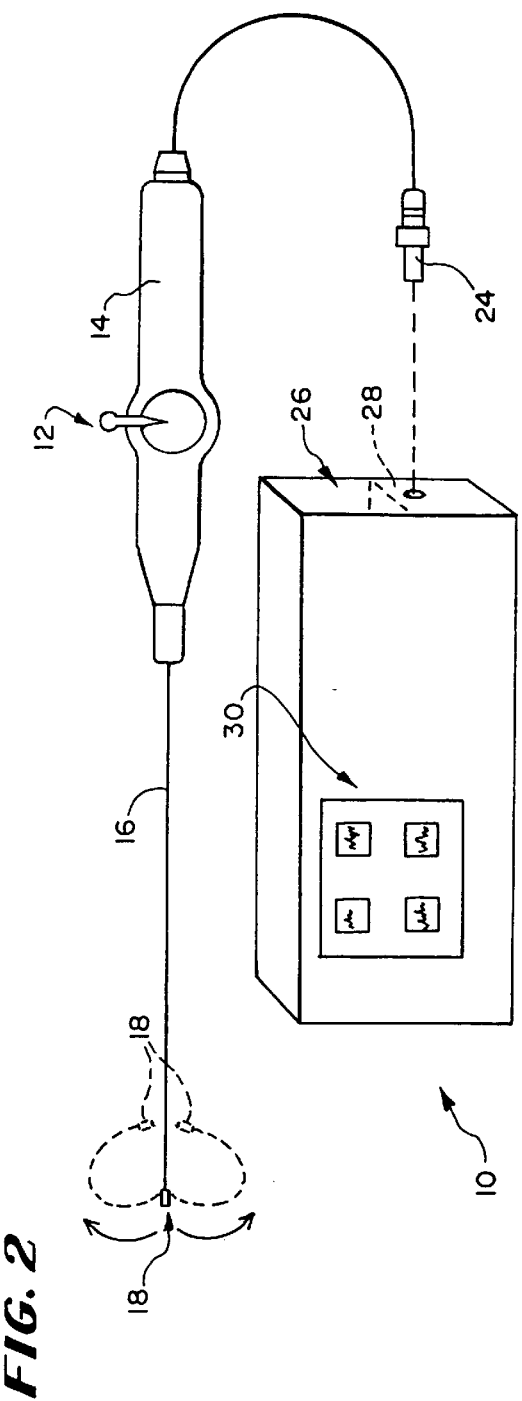
FIG. 2 is view of an electrode array carried by a catheter whose signals are processed by an associated controller to locate accessory pathways in the heart.

FIG. 2 shows a sensing system 10 that embodies the features of the invention. The system 10 includes a catheter 12. The catheter 12 includes a handle 14 and a guide body 16. The guide body 16 is made of a flexible plastic material, like Pebax or polyethylene. This material retains its shape and does not soften significantly at human body temperature.

The guide body 16 carries a handle 14 at its proximal end. The guide body 16 carries a sensing electrode array 18 at its distal end. The sensing array 18 detects electrical signals in heart tissue. If needed, the guide body 16 can employ a conventional catheter steering mechanism 20 to deflect and steer the electrode array 18 (as shown by phantom lines in FIG. 2).

A physician uses the sensing array 18 to detect electrophysiological events along the AV groove in the heart, with the objective to locate an accessory pathway (AP).

Figure 7:
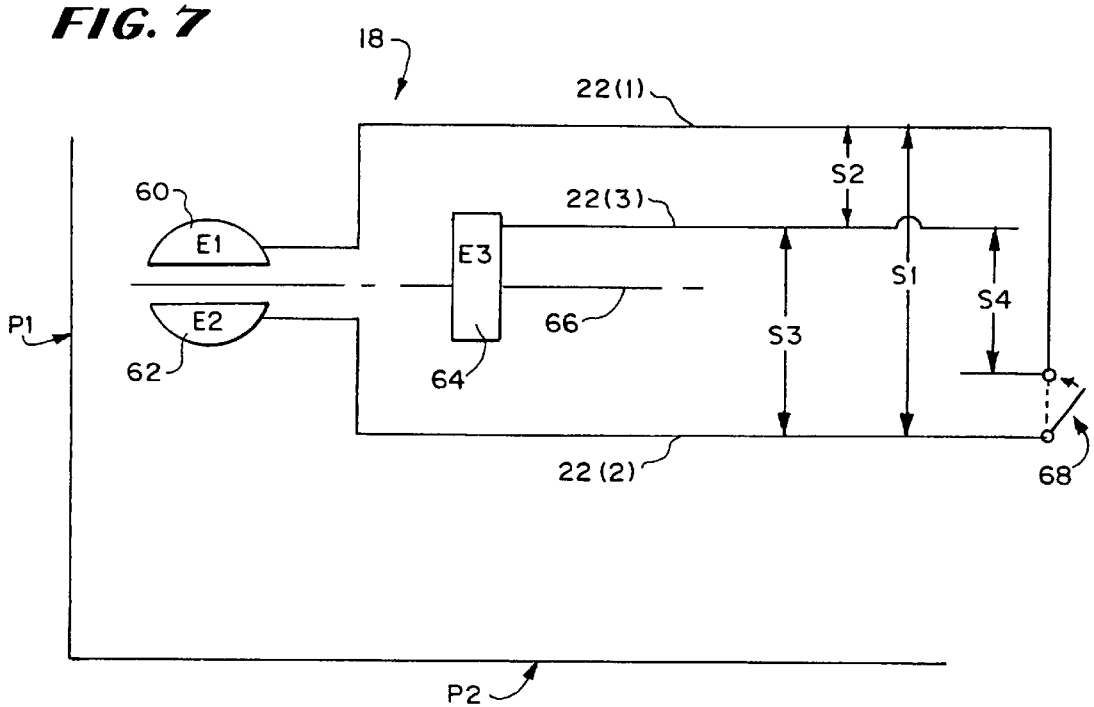
FIG. 7 is a diagrammatic view of the signal wires coupled to the multiple electrode array shown in FIGS. 4 to 6, being used to measure multiple bipolar signals along different orthogonal planes.

The sensing array 18 is electrically coupled to signal wires 22 (see FIG.7). The signal wires 22 extend through the guide body 16 into the handle 14. One or more connectors 24 attach the proximal ends of the signal wires to an input plug on a controller 26.

The controller 26 includes a signal monitor module 28. The signal monitor module 28 receives electrical signals detected by the sensing array 18. The signal monitor module processes the electrical signals.

The signal monitor module 28 drives a display device 30 on the controller 26. As will soon become apparent, the display device 30 presents an analysis of electrical activity in a format that the physician can readily view and interpret.

FIG. 3 shows a simplified and diagrammatic view of sensing array 18 in use within the interior structure of a human heart 32. It should be appreciated that the views of the heart shown in FIG. 3 and other Figures in this Specification are not intended to be anatomically accurate in every detail. The Figures show views of the heart in diagrammatic form as necessary to explain the features of the invention.

FIG. 3 shows the right and left right atria, respectively 34 and 36. FIG. 3 also shows the right and left ventricles, respectively 38 and 40. FIG. 3 further shows the atrial septum 42 that separates the right and left atria. FIG. 3 also shows the ventricular septum 44 that separates the right and left ventricles.

FIG. 3 also shows the fibrous structure of the AV groove separating the atria 34/36 from the ventricles 38/40. The tricuspid valve 48 is formed in the AV groove 46 between the right atrium 34 and right ventricle 38. The mitral (or bicuspid) valve 50 is,formed in the AV groove 46 between the left atrium 36 and the left ventricle 40.

The AV conduction system includes the sinoatrial node (or "SA node") 52, which generates an electrical impulse to begin normal sinus rhythm. In a normal heart, the impulse propagates uniformly across the right and left atria 34/36 and the atrial septum 42 to the atrioventricular (AV) groove 46, causing the atria 34/36 to contract.

The AV conduction system further includes the atrioventricular node (or "AV node") 54 and the bundle of HIS (or "HIS bundle") 56, through which the electrical impulse crosses over the AV groove 46 to the ventricles 38/40.

The AV node 54 first slows the conduction of the impulse, allowing the atria 34/36 to completely contract. The HIS bundle 56 then delivers the slowed impulse to the ventricles 38/40, causing them to contract after the atria 34/36.

FIG. 3 shows the location of an accessory pathway AP passing through the AV groove 46.

FIG. 3 shows the catheter guide body 16 maneuvered by the physician through a main vein or artery to bring the sensing array 18 into the interior region of the heart 32 (which is shown to be the right atrium 34). The sensing array 18 has been placed by the physician in contact with endocardial tissue along the AV groove 46.

FIGS. 4 to 6 show one preferred embodiment of the sensing array 18 in greater detail. The sensing array 18 includes an elongated body 58. The body 58 is formed of an inert, electrically nonconductive (i.e., dielectric) plastic material, like polyamide, polycarbonate, or styrene. The body 42 preferably has a modulus that lends both resilience and mechanical strength. Consequently, the body 42 can be maneuvered by the physician into stable and uniform contact with tissue along the AV groove (as FIG. 3 shows). In the embodiment shown in FIGS. 4 to 6, the body 58 carries three electrode elements 60, 62, and 64. The elements 60, 62, and 64 are made of a biocompatible, electrically conductive material. The first and second elements 60 and 62 are positioned at diametrically opposite sides of the distal tip of the body 58. The third element 64 encircles the body 58 away from the distal tip. The third element 64 takes the form of a ring.

The electrode elements 60, 62, and 64 can be made of a solid, electrically conducting material, like platinum or gold, attached to the body. The elements 60, 62, and 64 can be secured to the body 58 with a nonconducting adhesive material such as Loctite®.

Alternatively, the electrode elements 60, 62, and 64 can be formed by coating the exterior surface of the body 58 with an electrically conducting material, like platinum or gold. The coating can be applied using sputtering, ion beam deposition, or equivalent techniques.

The first, second, and third elements 60, 62, and 64 are electrically isolated from each other, being separated by the electrically nonconductive plastic material of the body 58.

As FIG. 7 shows diagrammatically, individual first, second, and third signal wires 22(1), 22(2), and 22 (3) are electrically connected to the first, second, and third electrode elements 60, 62, and 64, respectively. As before described, the signal wires 22(1)/(2)/(3) extend through the guide body 16 to the connector 24 that is plugged into the controller 26 (as FIG. 2 shows).

The array 18 comprises a compact arrangement of multiple, electrically independent electrodes (also designated E1, E2, and E3 in FIG. 7) that can sense electrical potentials in a bipolar mode. Operated in a bipolar mode, the electrodes E1, E2, and E3 sense multiple electrical potentials in multiple orthogonal planes (designated P1 and P2 in FIG. 7) without moving the array 18.

As FIG. 7 shows, the electrodes E1, E2, and E3 can provide as many as four different bipolar signal readings in two different orthogonal planes P1 and P2.

The first and second electrodes E1 and E2 provide a first bipolar signal reading (S1) in the first plane P1 transverse the catheter body axis 66.

The first and third electrodes E1 and E3 provide a second bipolar signal reading (S2) in the second plane P2 along the body axis 66.

Similarly, the second and third electrodes E2 and E3 provide a third bipolar signal (S3) reading in the second plane P2 along the body axis 66.

Furthermore, the first and second electrodes E1 and E2 can be electrically connected (through switch element 68), forming a unified tip electrode. A conventional fourth bipolar signal S4 can be obtained between the unified tip electrode and the third electrode E3 in the second plane P2 along the body axis 66.

In addition, if desired, the array 18 can provide three different unipolar readings between each electrode E1, E2, and E3 and an external indifferent electrode (not shown).

The size of each electrode element 60, 62, and 64 is selected to provide sensitivity to small volume signals in each orthogonal plane P1 and P2. Furthermore, the spacing among the elements 60, 62, and 64 is selected to reduce separation in the electrical potentials measured in each orthogonal plane P1 and P2.

In a preferred embodiment (see FIG. 4), the body 58 has a diameter of about 7-french (a french equals 0.33 mm). The first and second electrode elements 60 and 62 each measures about 4 mm in length. They are transversely separated by a distance (D1) of about 0.5 mm. The third electrode element 64 measures about 1 mm in length. It is axially separated from the first and second electrode elements 60 and 62 by a distance (D2) of about 2 mm.

Figure 8:
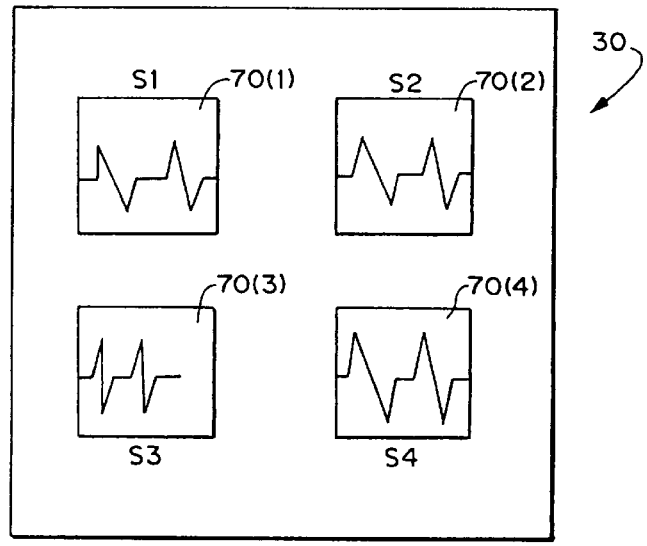
FIG. 8 is a display created by the controller shown in FIG. 2, showing the multiple bipolar signals as electrogram complexes.

As FIG. 8 best shows, the display device shows electrogram recordings for each of the four signal readings, designated 70(1), 70(2), 70(3), and 70(4) in FIG. 8. By comparing the morphologies of the electrogram signals 70(1)/(2)/(3)/(4), the physician can select the electrogram signal that provides the least time separation between the atrial potential A and ventricular potential V. This electrogram signal provides the best sensitivity to the small signals associated with the accessory pathway AP.

In FIG. 8, electrogram signal 70(3) shows the least separation. It is therefore selected.

The electrogram morphology on the display 30 also can be used by the physician to confirm uniform contact between the various electrode elements 60, 62, and 64 and the tissue along the AV groove 46. The physician can choose to orient the array 18 either orthogonal to the endocardial surface or planar against it, depending upon how much surface area along the groove 46 the physician wants to examine.

In use (as FIG. 9 shows), the physician moves the array 18 along the AV groove 46 from position A to B to C to D), While moving the array 18, the physician views changes in electrogram morphologies for the selected signal 70(3), as signals 70(3) A/B/C/D show in FIG. 9.

As FIG. 9 shows, as the array 18 moves closer to the site of the accessory pathway AP (at position D), the A–V signal time separation of the selected "best" electrogram decreases. Compare the signal 70(3) at array position A with the signal 70(3) at array positions B and C.

As the signal 70(3) at array position C shows, when the array 18 gets close enough to the pathway AP, the signal clarity that the selected "best" electrogram signal 70(3) provides will pick up the small volume activation potential signal from the accessory pathway AP itself. Due to its sensitivity and alignment, the "best" electrogram signal 70(3) will not lose the AP signal as the separation between the A and V signals lessens. Instead, the array 18 retains the signal isolation in the very localized area of the accessory pathway AP, to thereby differentiate between the AP signal and the ventricular V signal.

As electrogram signal 70(3) at position D shows, the atrial signal A and ventricular signal V merge at the site of the accessory pathway AP.

With this information, the physician can introduce a conventional ablation electrode (not shown) at the identified site to ablate it. Alternatively, using the sensing array embodiment shown in FIGS. 4 to 6, the physician can electrically connect the first and second electrodes 60 and 62 together, forming a unified ablation electrode that can apply radiofrequency ablation energy in association with an external indifferent electrode.

By improving the recording of the accessory pathway AP, the precise location of the pathway AP can be ablated. The success rate of the mapping and ablation procedure is thereby significantly improved.

EXAMPLE

An array 18 as shown in FIGS. 4 to 6 was used in vivo to record accessory AP pathways activation potentials at the ventricular insertion of left sided AP's. The first, second, and third bipolar signals S1, S2, and S3 sensed were compared to the conventional bipolar signal S4. The comparison between these signals was performed in 10 patients with an overt left free-wall AP.

In all patients, an AP potential could be recorded from the left ventricle during sinus rhythm with the conventional bipolar signal S4. However, in 8 of the 10 patients, the signal S4 fused the AP potential with the local V potential.

In contrast, using the first, second, and third signals S1, S2, and S3 taken according to the invention, the AP potential was always clearly separated from both the local A and local V potentials in all patients. Using the first, second, and third signals S1, S2, and S3, the time difference between the AP potential and the V potential was 28±8 milliseconds, due to a reduction in the width of the V potential. The width of the V potential in signals S1, S2, and S3 was 25+4 milliseconds, compared to a width of 53±18 milliseconds using the conventional bipolar electrode configuration (i.e., in signal S4).

Bipolar recordings from either the first and second tip elements 60/62 versus the third ring element 64 revealed in 6 patients that the AP potential could be recorded only between one tip element 60 or 62 and the element 64.

The Example shows that the array 18 made according to the invention allows for easy and unambiguous recording of AP potentials.

FIGS. 10 and 11 show an alternative embodiment for an array 72 made according to the invention. The array includes five electrically isolated electrode elements E1, E2, E3, E4, and E5. The first, second, and third electrode elements E1, E2, and E3 are as previously described (as FIGS. 4 to 6 show). The array in FIGS. 10 and 11 include additional fourth and fifth electrode elements E4 and E5 positioned at diametrically opposite sides of the body 58 between the first and second elements E1/E2 and the third element E3.

Figure 12:
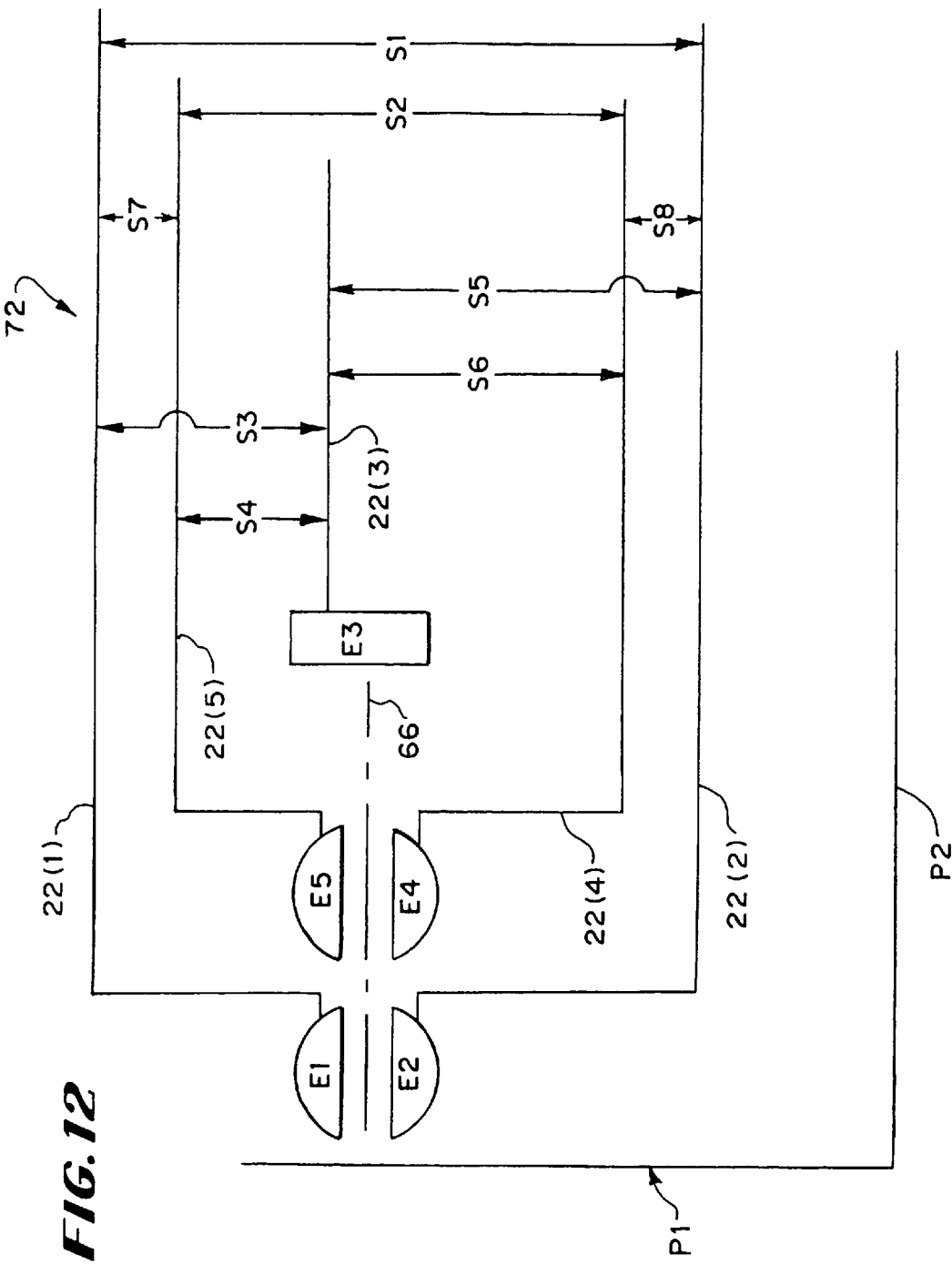
FIG. 12 is a diagrammatic view of the signal wires coupled to the multiple electrode array shown in FIGS. 10 and 11, being used to measure multiple bipolar signals along different orthogonal planes.

As FIG. 12 shows, individual signal wires 22(1) to 22(5) are connected to each elegctrode E1 to E5.

In one preferred assembly of the array 72 shown in FIGS. 10 and 11, the array body 58 has a diameter of 7-french. The first, second, fourth, and fifth electrode elements E1, E2, E4, and E5 each measures about 4 mm in length. They are separated in a transverse direction D1 along opposite side of the body by about 0.5 mm. The first and second elements E1 and E2 are separated from the third and fourth elements by an axial distance D3 of about 1 mm. The third element E3 measures about 2 mm in length. It is axially separated from the fourth and fifth electrode elements by an axial distance D2 of about 2.5 mm.

As FIG. 12 shows, the array 72 can be operated in a bipolar mode to provide as many as eleven different signal readings in two different orthogonal planes P1 and P2.

The first and second electrode elements E1 and E2 provide a first bipolar signal reading S1 in the a first plane P1 transverse the body axis 66. The fourth and fifth electrode elements E4 and E5 likewise provide a second bipolar signal S2 reading in the first plane P1.

The first and third electrode elements E1 and E3 provide a third bipolar signal reading S3 in the second plane P2 along the body axis 66. The fifth and third electrode elements E5 and E3 likewise provide a fourth bipolar signal reading S4 in the second plane P2.

The second and third electrode elements E2 and E3 provide a fifth bipolar signal reading S5 in the second plane P2 along the body axis 66. Similarly, the fourth and third electrode E4 and E3 elements provide a sixth bipolar signal reading S6 in the second plane P2.

The first and fifth electrode elements E1 and E5 provide a seventh bipolar signal reading S7 in the second plane P2, just as the second and fourth elements E2 and E4 provide an eighth bipolar signal reading S8 in the second plane P2.

Furthermore, the first/second electrodes E1/E2; fourth/fifth electrodes E4/E5; and first/second/fourth/fifth electrodes E1/E2/E4/E5 can be electrically connected, forming three unified tip electrode arrangements. Three additional bipolar signals S9, S10, and S11 (not shown in FIG. 12) can be obtained between the unified tip electrode arrangements and the third electrode element E3 in the second plane P2 along the body axis 66.

The array 72 provides additional electrode pairs that are sensitivity to small volume signals in each orthogonal plane P1 and P2. The multiple electrode pairs in the array 72 provide reduced separation in the electrical potentials measured in each orthogonal plane P1 and P2, compared with conventional bipolar sensing electrodes.

The features of the invention are set forth in the following claims.

We claim:

1. A method of sensing atrial and ventricular electrical potentials in heart tissue to locate the site of an accessory pathway on the AV groove, comprising:

establishing a contact site between heart tissue along the AV groove and an electrode array that includes a support body that carries a plurality of electrodes along generally perpendicular axes for sensing electrical potentials in heart tissue, the electrodes being electrically isolated from each other on the support body, continuously maintaining the site of contact between the electrode array and heart tissues, while measuring a plurality of bipolar signals, selecting an electrogram complex with the least time separation between the atrial potential signal and ventricular potential signal, advancing the site of contact of the electrode array in sequence along the AV groove to decrease the time separation between the atrial potential signal and ventricular potential signal in the selected electrogram complex until the atrial potential signal and ventricular potential signal in the selected electrogram complex merge, and identifying the site of contact of the electrode array where the atrial potential signal and ventricular potential signal in the selected electrogram complex merge as the site of the accessory pathway site.

2. A method according to claim 1 and further including the step of introducing an ablation electrode at the identified accessory pathway site and transmitting ablation energy through the ablation electorode to ablate the accessory pathway.

3. A method according to claim 1 and further including electrically connecting the first and second electrodes together to form a unified ablation electrode at the identified accessory pathway site, and transmitting ablation energy through the unified ablation electrode to ablate the accessory pathway.

* * * * *